United States Patent
Palushi et al.

(10) Patent No.: US 11,944,758 B2
(45) Date of Patent: Apr. 2, 2024

(54) ATRAUMATIC TIP ASSEMBLY FOR GUIDEWIRE

(71) Applicant: Acclarent, Inc., Irvine, CA (US)

(72) Inventors: Jetmir Palushi, Irvine, CA (US); Fatemeh Akbarian, Rancho Palos Verdes, CA (US); Henry F. Salazar, Pico Rivera, CA (US); Madison K Vanosdoll, Irvine, CA (US)

(73) Assignee: Acclarent, Inc., Irvine, CA (US)

( * ) Notice: Subject to any disclaimer, the term of this patent is extended or adjusted under 35 U.S.C. 154(b) by 566 days.

(21) Appl. No.: 17/099,877

(22) Filed: Nov. 17, 2020

(65) Prior Publication Data
US 2021/0178115 A1   Jun. 17, 2021

Related U.S. Application Data

(60) Provisional application No. 62/948,549, filed on Dec. 16, 2019.

(51) Int. Cl.
*A61M 25/00* (2006.01)
*A61B 5/00* (2006.01)
*A61M 25/09* (2006.01)

(52) U.S. Cl.
CPC ...... *A61M 25/001* (2013.01); *A61M 25/0012* (2013.01); *A61M 25/0068* (2013.01);
(Continued)

(58) Field of Classification Search
CPC .... A61M 25/0012; A61M 2025/09108; A61M 25/09; A61M 2025/09058–09091;
(Continued)

(56) References Cited

U.S. PATENT DOCUMENTS 4,846,186 A * 7/1989 Box ............... A61M 25/09
                                                600/585
7,720,521 B2   5/2010 Chang et al.
(Continued)

FOREIGN PATENT DOCUMENTS

WO   WO 2016/171940 A1   10/2016
WO   WO 2018/175412 A1    9/2018

OTHER PUBLICATIONS

International Search Report and Written Opinion dated Mar. 10, 2021, for International Application No. PCT/IB2020/061369, 20 pages.

*Primary Examiner* — Matthew P Travers
(74) *Attorney, Agent, or Firm* — Frost Brown Todd LLP

(57) ABSTRACT

A method is used to manufacture a surgical guidewire that includes an outer coil assembly, a position sensor, a communication wire, an adhesive, a core wire, a hollow tube, and an atraumatic tip. The outer coil assembly has an outer coil that extends distally from a proximal coil retainer to a distal coil retainer. The position sensor is located distally within the outer coil assembly and is configured to be in communication with a processor via the communication wire. The core wire is between an outer coil proximal portion and the hollow tube. A distal end of the hollow tube is bonded to the atraumatic tip. The method includes affixing the atraumatic tip to the distal end of the hollow tube with the adhesive. The adhesive is constructed of instant glue.

17 Claims, 15 Drawing Sheets

(52) U.S. Cl.
CPC ............ *A61M 25/09* (2013.01); *A61B 5/6851* (2013.01); *A61M 2025/09083* (2013.01); *A61M 2025/09108* (2013.01); *A61M 2025/09175* (2013.01); *A61M 2205/02* (2013.01)

(58) Field of Classification Search
CPC ....... A61M 2025/09175; A61B 5/6851; A61B 2017/00526; A61B 2034/2051
See application file for complete search history.

(56) References Cited

U.S. PATENT DOCUMENTS

| | | | |
|---|---|---|---|
| 8,023,675 B2 | 9/2011 | Tilson et al. | |
| 8,409,114 B2 | 4/2013 | Parins | |
| 9,155,492 B2 | 10/2015 | Jenkins et al. | |
| 9,757,018 B2 | 9/2017 | Kesten et al. | |
| 9,931,047 B2 | 4/2018 | Srivastava | |
| 10,463,242 B2 | 11/2019 | Kesten et al. | |
| 10,561,370 B2 | 2/2020 | Salazar et al. | |
| 10,610,308 B2 | 4/2020 | Sema et al. | |
| 2009/0036833 A1* | 2/2009 | Parins | A61M 25/00 604/525 |
| 2010/0228150 A1 | 9/2010 | Zimmerman et al. | |
| 2012/0046575 A1* | 2/2012 | Brown | A61M 25/09 600/585 |
| 2012/0172761 A1* | 7/2012 | Meller | A61B 5/6851 600/585 |
| 2013/0267934 A1* | 10/2013 | Eskuri | A61M 25/09 604/528 |
| 2014/0364725 A1 | 12/2014 | Makower | |
| 2015/0142041 A1 | 5/2015 | Kendale et al. | |
| 2016/0310041 A1* | 10/2016 | Jenkins | A61B 17/24 |
| 2018/0000420 A1 | 1/2018 | Romanowski et al. | |
| 2018/0098850 A1 | 4/2018 | Rafiee et al. | |
| 2018/0098871 A1 | 4/2018 | Sasse et al. | |
| 2018/0140302 A1 | 5/2018 | Pai et al. | |
| 2019/0090890 A1 | 3/2019 | Kugler et al. | |
| 2020/0222067 A1* | 7/2020 | Gill | A61B 17/22 |

\* cited by examiner

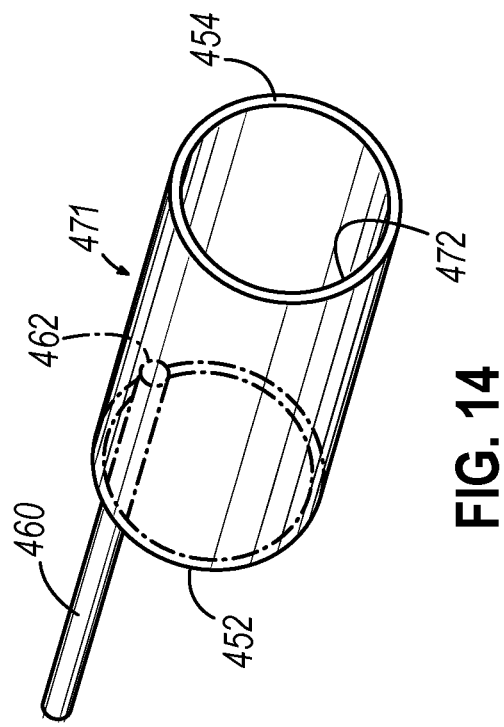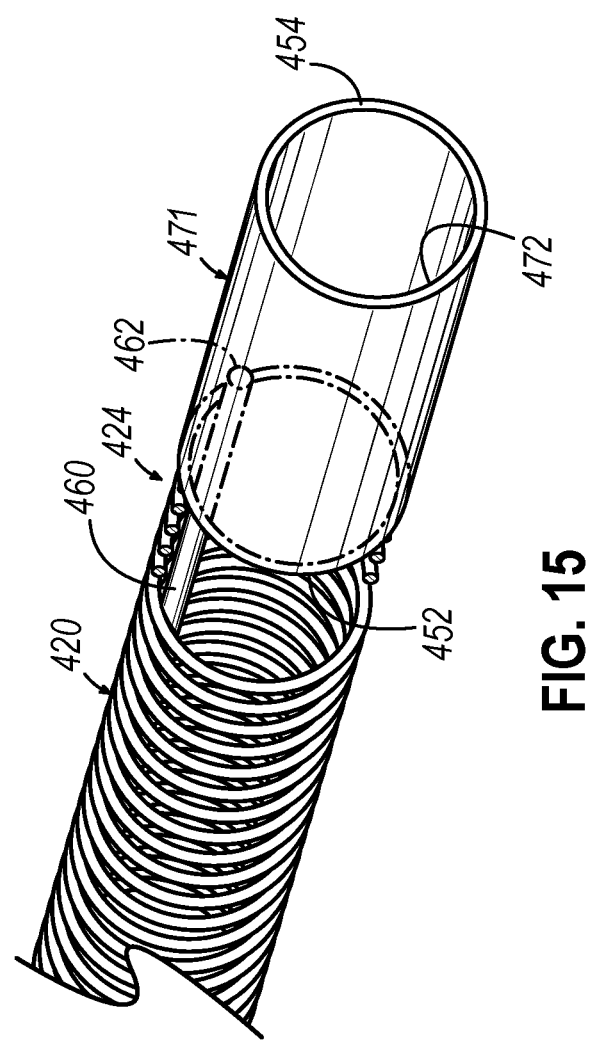

ATRAUMATIC TIP ASSEMBLY FOR GUIDEWIRE

PRIORITY

This application claims the benefit of U.S. Provisional Pat. App. No. 62/948,549, filed Dec. 16, 2019, entitled "Atraumatic Tip Assembly for Guidewire," the disclosure of which is incorporated by reference herein.

BACKGROUND

Surgical instruments such as surgical guidewires facilitate operations within or adjacent to an anatomical passageway of a patient's body. Surgical guidewires are thin, flexible, medical wires inserted into the body of a patient to guide a larger instrument such as a catheter, a central venous line, or a feeding tube for an operation within the body.

In some instances, a combination of a guidewire and catheter is used to position an inflatable balloon within the anatomical passageway. The balloon is inflated with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus.

Guidewires may include a blunt or rounded atraumatic tip that prevents the guidewire from gouging or damaging the tissue within the body when the distal end is inserted along an anatomical passageway of the body. The atraumatic tip may be constructed of epoxy and then be bonded to the guidewire with a metered amount of glue. The specific amount of glue may be difficult to monitor. The epoxy may require either an extended period of time or an oven to dry properly. When the guidewire is used with a dilation catheter that has a balloon, the diametric tolerances must be within strict limits. Otherwise, the atraumatic epoxy tip may undesirably engage the inner lumen of the catheter and detach from the guidewire.

Once a surgical guidewire is constructed, an operator may insert the distal end of the guidewire within the body such as through a nostril or a mouth of a patient toward a desired location within the patient. With the distal end of the elongate shaft inserted within the patient, an operator may manipulate the guidewire to carry the larger instrument such as a catheter through the anatomical passageway of a patient in an unobstructed and non-damaging manner, while referencing the location of the guidewire by use of a position sensor and an image-guided surgery (IGS) system.

IGS is a technique where a computer is used to obtain a real time correlation of the location of an instrument that has been inserted into a patient's body to a set of preoperatively obtained images (e.g., a CT or Mill scan, 3-D map, etc.) so as to superimpose the current location of the instrument on the preoperatively obtained images. In some IGS procedures, a digital tomographic scan (e.g., CT or Mill, 3-D map, etc.) of the operative field is obtained prior to surgery. A specially programmed computer is then used to convert the digital tomographic scan data into a digital map. During surgery, special instruments having sensors (e.g., electromagnetic coils that emit electromagnetic fields and/or are responsive to externally generated electromagnetic fields) mounted thereon are used to perform the procedure while the sensors send data to the computer indicating the current position of each surgical instrument. The computer correlates the data it receives from the instrument-mounted sensors with the digital map that was created from the preoperative tomographic scan. The tomographic scan images are displayed on a video monitor along with an indicator (e.g., cross hairs or an illuminated dot, etc.) showing the real time position of each surgical instrument relative to the anatomical structures shown in the scan images. In this manner, the surgeon is able to know the precise position of each sensor-equipped instrument by viewing the video monitor even if the surgeon is unable to directly visualize the instrument itself at its current location within the body. An example of an electromagnetic IGS system that may be used in ENT and sinus surgery includes the CARTO® 3 System by Biosense Webster, Inc., of Irwindale, California.

When applied to functional endoscopic sinus surgery (FESS), balloon sinuplasty, and/or other ENT procedures, the use of image guidance systems allows the surgeon to achieve more precise movement and positioning of the surgical instruments than can be achieved by viewing through an endoscope alone. This is so because a typical endoscopic image is a spatially limited, 2-dimensional, line-of-sight view. The use of image guidance systems provides a real time, 3-dimensional view of all of the anatomy surrounding the operative field, not just that which is actually visible in the spatially limited, 2-dimensional, direct line-of-sight endoscopic view. As a result, image guidance systems may be particularly useful during performance of FESS, balloon sinuplasty, and/or other ENT procedures where a section and/or irrigation source may be desirable, especially in cases where normal anatomical landmarks are not present or are difficult to visualize endoscopically.

It may be desirable to efficiently manufacture surgical guidewires that include atraumatic tips. While several different methods to manufacture surgical guidewires have been used, and surgical guidewires have been made it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 14 depicts a perspective view of a proximal hypotube of the hypotube assembly of FIG. 13, shown in phantom for greater clarity, having a core wire soldered to the proximal hypotube;

FIG. 15 depicts a perspective view of the hypotube assembly and core wire of FIG. 14 positioned at a distal end of an outer coil assembly;

Figure 1:
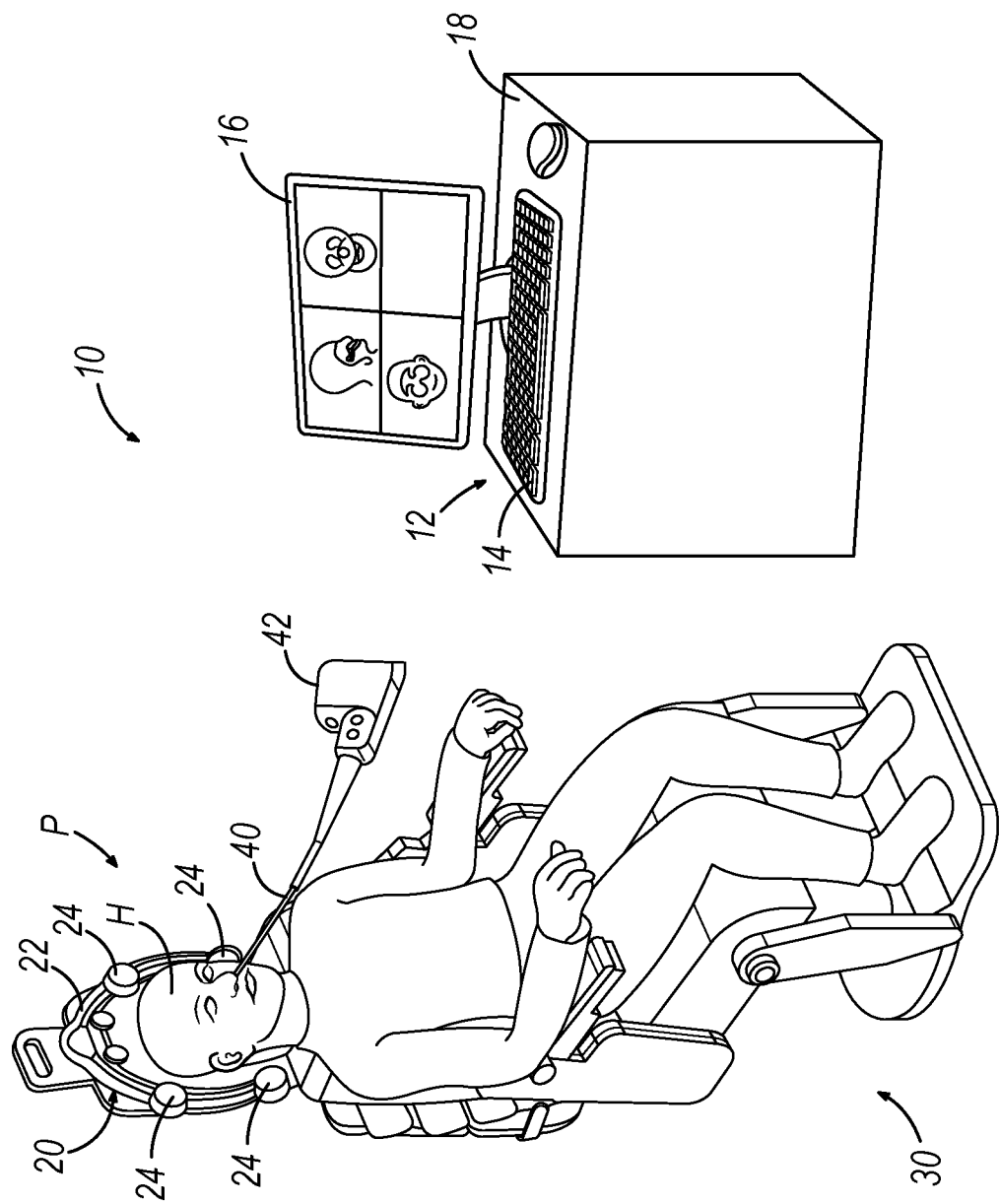
FIG. 1 depicts a schematic view of an exemplary surgery navigation system being used on a patient seated in an exemplary medical procedure chair.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "axial," and "longitudinal" also are used herein for reference to relative positions and directions. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Exemplary Image Guided Surgery Navigation System

When performing a medical procedure within a head (H) of a patient (P), it may be desirable to have information regarding the position of an instrument within the head (H) of the patient (P), particularly when the instrument is in a location where it is difficult or impossible to obtain an endoscopic view of a working element of the instrument within the head (H) of the patient (P). FIG. 1 shows an exemplary IGS navigation system (10) enabling an ENT procedure to be performed using image guidance. In addition to or in lieu of having the components and operability described herein IGS navigation system (10) may be constructed and operable in accordance with at least some of the teachings of U.S. Pat. No. 7,720,521, entitled "Methods and Devices for Performing Procedures within the Ear, Nose, Throat and Paranasal Sinuses," issued May 18, 2010, the disclosure of which is incorporated by reference herein; and U.S. Pat. Pub. No. 2014/0364725, entitled "Systems and Methods for Performing Image Guided Procedures within the Ear, Nose, Throat and Paranasal Sinuses," published Dec. 11, 2014, now abandoned, the disclosure of which is incorporated by reference herein.

IGS navigation system (10) of the present example comprises a field generator assembly (20), which comprises set of magnetic field generators (24) that are integrated into a horseshoe-shaped frame (22). Field generators (24) are operable to generate alternating magnetic fields of different frequencies around the head (H) of the patient (P). A navigation guidewire (40) is inserted into the head (H) of the patient (P) in this example. Navigation guidewire (40) may be a standalone device or may be positioned on an end effector or other location of a medical instrument such as a surgical cutting instrument or dilation instrument. In the present example, frame (22) is mounted to a chair (30), with the patient (P) being seated in the chair (30) such that frame (22) is located adjacent to the head (H) of the patient (P). By way of example only, chair (30) and/or field generator assembly (20) may be configured and operable in accordance with at least some of the teachings of U.S. Pat. No. 10,561,370, entitled "Apparatus to Secure Field Generating Device to Chair," issued Feb. 18, 2020, the disclosure of which is incorporated by reference herein.

IGS navigation system (10) of the present example further comprises a processor (12), which controls field generators (24) and other elements of IGS navigation system (10). For instance, processor (12) is operable to drive field generators (24) to generate alternating electromagnetic fields; and process signals from navigation guidewire (40) to determine the location of a position sensor (not shown) in navigation guidewire (40) within the head (H) of the patient (P). Processor (12) comprises a processing unit communicating with one or more memories. Processor (12) of the present example is mounted in a console (18), which comprises operating controls (14) that include a keypad and/or a pointing device such as a mouse or trackball. A physician uses operating controls (14) to interact with processor (12) while performing the surgical procedure.

Navigation guidewire (40) includes a position sensor that is responsive to positioning within the alternating magnetic fields generated by field generators (24). A coupling unit (42) is secured to the proximal end of navigation guidewire (40) and is configured to provide communication of data and other signals between console (18) and navigation guidewire (40). Coupling unit (42) may provide wired or wireless communication of data and other signals.

In the present example, the position sensor of navigation guidewire (40) comprises at least one coil at the distal end of navigation guidewire (40). When such a coil is positioned within an alternating electromagnetic field generated by field generators (24), the alternating magnetic field may generate electrical current in the coil, and this electrical current may be communicated along the electrical conduit(s) in navigation guidewire (40) and further to processor (12) via coupling unit (42). This phenomenon may enable IGS navigation system (10) to determine the location of the distal end of navigation guidewire (40) or other medical instrument (e.g., dilation instrument, surgical cutting instrument, etc.) within a three-dimensional space (i.e., within the head (H) of the patient (P), etc.). To accomplish this, processor (12) executes an algorithm to calculate location coordinates of the distal end of navigation guidewire (40) from the position related signals of the coil(s) in navigation guidewire (40). While the position sensor is located in guidewire (40) in this example, such a position sensor may be integrated into various other kinds of instruments, including those described in greater detail below.

Processor (12) uses software stored in a memory of processor (12) to calibrate and operate IGS navigation system (10). Such operation includes driving field generators (24), processing data from navigation guidewire (40), processing data from operating controls (14), and driving display screen (16). In some implementations, operation may also include monitoring and enforcement of one or more safety features or functions of IGS navigation system (10). Processor (12) is further operable to provide video in real time via display screen (16), showing the position of the distal end of navigation guidewire (40) in relation to a video camera image of the patient's head (H), a CT scan image of the patient's head (H), and/or a computer generated three-dimensional model of the anatomy within and adjacent to the patient's nasal cavity. Display screen (16) may display such images simultaneously and/or superimposed on each other during the surgical procedure. Such displayed images may also include graphical representations of instruments that are inserted in the patient's head (H), such as navigation guidewire (40), such that the operator may view the virtual rendering of the instrument at its actual location in real time. By way of example only, display screen (16) may provide images in accordance with at least some of the teachings of U.S. Pat. No. 10,463,242, entitled "Guidewire Navigation for Sinuplasty," issued Nov. 5, 2019, the disclosure of which is incorporated by reference herein. In the event that the operator is also using an endoscope, the endoscopic image may also be provided on display screen (16).

The images provided through display screen (16) may help guide the operator in maneuvering and otherwise manipulating instruments within the patient's head (H) when such instruments incorporate navigation guidewire (40). It should also be understood that other components of a surgical instrument and other kinds of surgical instruments, as described below, may incorporate a position sensor like the position sensor of navigation guidewire (40).

II. Exemplary Surgical Guidewire with Atraumatic Tip

FIGS. 2-8 depict an example of a guidewire (100) that incorporates a position sensor (130) similar to the position sensor (not shown) of guidewire (40) described above. Like the position sensor of guidewire (40), position sensor (130) helps guide the operator in maneuvering within the patient's head (H) by providing signals indicating the position of guidewire (100) within the patient's head (H) in real time. Guidewire (100) is unlike guidewire (40) in that guidewire (100) has an atraumatic tip (110) that is formed and attached in accordance with the teachings below. The guidewire (100) has features that allow a manufacturer to accurately and efficiently install the atraumatic tip (110) in a manner that may reduce the time needed to inspect the installed the atraumatic tip (110), reduce the price of materials, and/or reduce the skill and time needed to install the atraumatic tip (110).

Guidewire (100) may be used to guide a larger instrument such as a catheter, a central venous line, or a feeding tube for an operation within or adjacent to various different anatomical passageways of the body. More specifically, and by way of example only, the guidewire (100) may be used within the frontal sinus ostium, frontal recess, maxillary sinus ostium, sphenoid sinus ostium, ethmoid sinus ostium, Eustachian tube, etc. The guidewire (100) of the present example includes an outer coil assembly (120), a position sensor (130), a communication wire (140), an adhesive (150), a core wire (160), a hypotube (170), and the atraumatic tip (110).

The outer coil assembly (120) generally includes an outer coil (122) that extends from a proximal coil retainer (180) to a distal coil retainer (190). The outer coil (122) has a helically wound coil stock (121) that extends distally throughout the length of the outer coil (122). The coil stock (121) has a set number of turns per length throughout the length of the outer coil (122). The coil stock (121) may also vary the number of turns per length. For example, an outer coil distal and proximal portions (124, 126) may have more turns per length than the coil stock (121) between the outer coil distal and proximal portions (124,126). Increasing the number of turns per length stiffens the outer coil (122) in the outer coil distal and proximal portions (124,126). The coil stock (121) is constructed of a surgical safe metal such as aluminum or stainless steel. The coil stock (121) has resilient yet flexible properties. The outer coil (120) further includes a bend (123) formed proximate and proximal to an outer coil distal portion (124). The bend (123) may be bent at an angle in accordance with bend angles known in the art of guidewires that are used in ENT surgical procedures.

The proximal coil retainer (180) has an annular shape and encompasses the outer coil proximal portion (126). The proximal coil retainer (180) may be constructed of a surgically safe metal or plastic. The proximal coil retainer (180) is sized to tightly fit around the outer coil proximal portion (126). The proximal coil retainer (180) has a retainer (not shown), a proximal face (not shown), a retainer distal face (not shown), a proximal retainer outside diameter (182), and a proximal retainer inside diameter (not shown). The proximal face (not shown) may be located proximal to the operator. The proximal coil retainer (180) extends distally with the outer coil proximal portion (126) attached coaxially within the proximal retainer inside diameter (not shown), and the outside diameter (182) has a surface configured to be gripped by an operator.

The outer coil proximal portion (126) has a coil stock end (not shown) that is generally similar to the end of a coil spring. The coil stock ends may be tapered so that the proximal coil retainer (180) fits squarely against the distal face (not shown) of the proximal coil retainer (180). Alternatively, the coil stock ends may terminate in or at the proximal coil retainer (180) without a taper. The proximal coil retainer (180) is operatively attached to the outer coil proximal portion (126). The proximal coil retainer (180) may include a thread (not shown) within in proximal retainer inside diameter (not shown), may include an adhesive, or may include a fastener (not shown) to retain the outer coil proximal portion (126). Other suitable methods to axially and radially fasten the proximal coil retainer (180) to the outer coil proximal portion (126) will be apparent to those skilled in the art in view of the teachings herein.

The proximal coil retainer (180) prevents the operator from touching the proximal end of the outer coil (122) which may be sharp or jagged. The proximal coil retainer (180) optionally may have a grommet (not shown) fitted within the proximal coil retainer (180). The grommet is configured to protect the communication wire (140) that runs through the proximal coil retainer (180). The proximal coil retainer (180) is also configured so that it cannot be pulled off the outer coil assembly (120) when an operator pulls proximally upon the proximal coil retainer (180). An operator may pull the proximal coil retainer (180) proximally to retract the outer coil assembly (120) from a body (B) of a patient (P). The proximal coil retainer (180) is configured to allow the operator to grip the outer coil assembly (120) to control the guidewire (100) while navigating the guidewire (100) through the body of the patient (P).

The outer coil distal portion (124) is operatively attached to the distal coil retainer (190) in a manner similar to the attachment of the proximal coil retainer (180) to the outer coil proximal portion (126). The distal coil retainer (190) has a distal retainer distal face (192), a distal retainer outside diameter (196), and a distal retainer inside diameter (198). The distal coil retainer (190) may be threaded within the distal retainer inner diameter (198). The distal coil retainer (190) may be glued to the distal retainer distal face (192) or the distal coil retainer (190) may be affixed with a fastener (128). Other suitable methods to axially and radially fasten the distal coil retainer (190) to the outer coil distal portion (124) will be apparent to those skilled in the art in view of the teachings herein.

The distal coil retainer (190) has an annular shape and encompasses an outer coil distal portion (124) and extends distally from an outer coil distal portion (124) to the hypotube (170). The edges (191) of the distal coil outside diameter (196) may be chamfered or rounded to facilitate the sliding of the guidewire (100) through the body. The distal coil retainer (190) differs from the proximal coil retainer (180) in that the distal coil retainer (190) has a provision (not shown) for attaching the hypotube (170). The provision may include a hypotube retainer, an adhesive, or some other fastener that allows the distal coil retainer (190) to axially and radially fasten the distal coil retainer (190) to the hypotube (170). Examples of the provision for attaching the hypotube (170) to distal coil retainer (190) will be apparent to those skilled in the art in view of the teachings herein. In some versions, an adhesive (150) such as an instant glue is used to attach the hypotube (170) to distal coil retainer (190). The distal coil retainer (190) may additionally have a recess (not shown) located at the distal end of the distal coil retainer (190). The recess (not shown) may be configured to allow the hypotube (170) to be centrally positioned within the recess (not shown) to aid in centering and retaining the hypotube (170) in distal coil retainer (190).

The hypotube (170) is a hollow tube that distally extends from the distal coil retainer (190) to an adhesive (150) that affixes the atraumatic tip (110) to the hypotube (170). The hypotube (170) is constructed of a surgically safe metal such as stainless steel, a nickel titanium alloy, tantalum, niobium, or other metallic material capable of being welded, soldered, or brazed.

The position sensor (130) is located within the hypotube inner diameter (172). The position sensor (130) is in communication with the processor (12) via the communication wire (140). The position sensor (130) may include one or more coils. The position sensor (130) is configured to generate signals in response to an alternating electromagnetic field generated by field generators (24), with such signals being indicative of the location of position sensor (130) (and, hence, the distal end of guidewire (100)) within the head (H) of the patient (P). The communication wire (140) is operatively affixed to the position sensor (130) and runs from the position sensor (130) to the processor (12). The position sensor (130) thus helps an operator determine the position of the distal tip of the guidewire (100) relative to the patient's body.

In the current example, the hypotube (170) is affixed to the core wire (160) within a hypotube inside diameter (172). The core wire distal end (162) is soldered, brazed or welded to the hypotube inside diameter (172) and the core wire proximal end (164) is affixed to the outer coil proximal portion (126). Alternately, the core wire (160) also may be affixed to the proximal coil retainer (180).

The core wire (160) may be constructed of a stainless steel, or any material that is non-extensible and surgically safe. Various suitable materials that may be used to form core wire (160) will be apparent to those skilled in the art in view of the teachings herein. The core wire (160) is configured to provide two functions. The core wire (160) is configured to be a tether for the hypotube (170) and provide tensile strength for the outer coil (122) along the length of the outer coil assembly (120). The core wire (160) further secures the hypotube (170) relative to the distal coil retainer (190). In the event that the hypotube (170) becomes undesirably detached from the distal coil retainer (190) while in the body of the patient (P), the core wire (160) prevents the hypotube (170) from getting lost in the body of the patient (P). The core wire (160) keeps the outer coil (122) from longitudinally expanding the helical shape of the coil stock (121) if the guidewire (100) is pulled proximally while a resistance holds the distal end of the guidewire (100). Tortuous anatomical passageways of the body may produce the resistance that holds the distal end of the guidewire (100). The non-extensible core wire (160) will not allow the coil stock (121) to expand beyond the length of the core wire (160).

Figure 9:
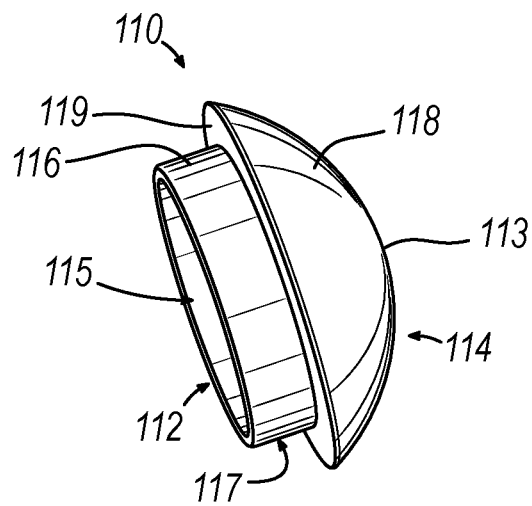
FIG. 9 depicts an enlarged perspective view of the atraumatic tip of FIG. 7.

The atraumatic tip (110) includes a proximal tip portion (112) (see FIG. 9) and a distal tip portion (114) (see FIG. 9). The proximal tip portion (112) is in the form of a shaft (116) (see FIG. 9) that is inserted within the hypotube inner diameter (172). The atraumatic tip (110) may include a hollow shaft (116) (see FIG. 9). The distal tip portion (114) (see FIG. 9) has an arcuate portion (118) (see FIG. 9) and a proximal face (119) (see FIG. 9). The adhesive (150) is applied between the proximal face (119) (see FIG. 9) and the hypotube distal face (176). The adhesive (150) may also be located between the distal portion of the hypotube inner diameter (172) and the proximal tip portion (112) (see FIG. 9). The adhesive (150) may be constructed of an instant glue (150).

In some instances, atraumatic tip (not shown) may include an optical fiber extending into a distal illuminating tip (not shown). By way of example only, guidewire (100) may be configured in accordance with at least some of the teachings of U.S. Pat. No. 9,155,492, entitled "Sinus Illumination Lightwire Device," issued on Oct. 13, 2015; U.S. Pat. No. 9,757,018, entitled "Medical Guidewire with Integral Light Transmission," issued on Sep. 12, 2017; and U.S. Pat. No. 10,610,308, entitled "Navigation Guidewire with Interlocked Coils," issued on Apr. 7, 2020, the disclosures of which is incorporated by reference herein.

III. Assembly of Exemplary Guidewire with Atraumatic Tip

Figure 4:
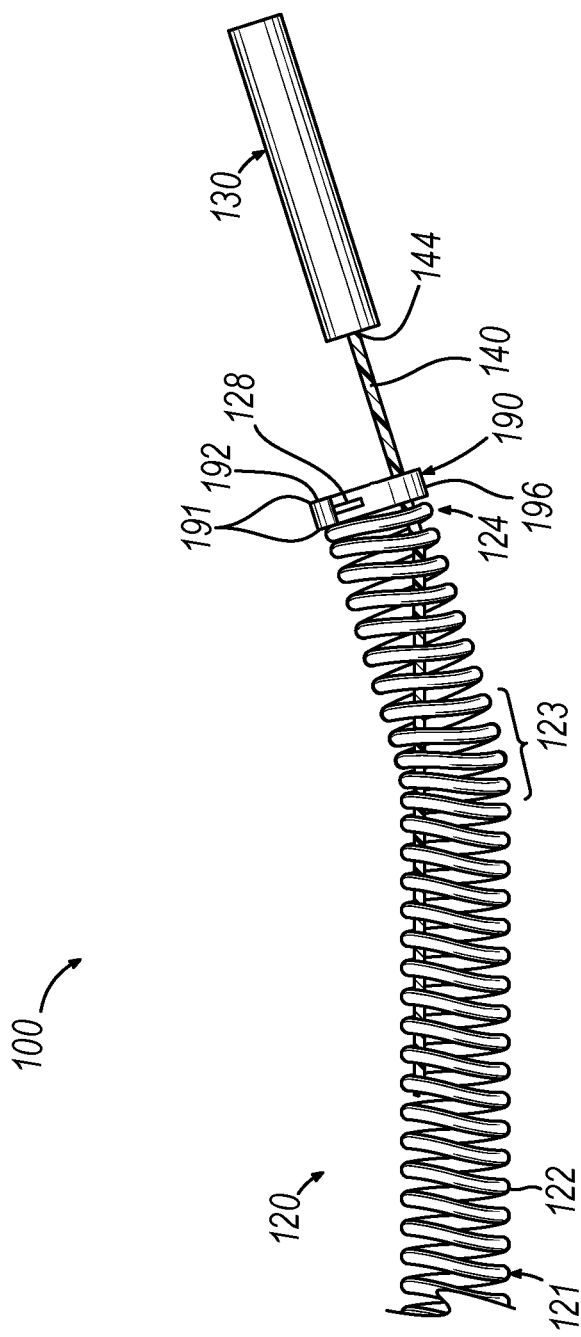
FIG. 4 depicts an enlarged side elevational view of the guidewire of FIG. 2 during an initial state of assembly where the guidewire is being fitted with a position sensor.

FIG. 4 shows the outer coil distal portion (124) fitted with the distal coil retainer (190). The distal end of the communication wire (144) is connected to the position sensor (130) by soldering the communication wire (140) before the position sensor (130) is inserted proximally into the outer coil assembly (120). The communication wire (140) is then fed proximally through the distal coil retainer (190), through the outer coil (122) and further through the proximal coil retainer (180). The proximal end of the communication wire (142) is connected to the processor (12). In some instances, the proximal end of the communication wire (142) may be connected to a coupling unit (not shown). The coupling unit may be configured to provide wireless (or wired) communication of data and other signals between processor (12) and navigation guidewire (100) similar to coupling unit (42) (see FIG. 1). The coupling unit may be secured to the proximal end of the navigation guidewire (100).

In some instances, the communication wire (140) may be connected to a wiring connector (not shown), and the wiring connector may be connected with the processor (12) or the coupling unit (not shown). The position sensor (130) may have a connector (not shown) that is fitted to the communication wire (140) to further simplify the assembly process and protect the position sensor (130) from the heat associated with soldering. Other ways to connect the position sensor (130) to the communication wires (140) would be apparent to one skilled in the art in view of the teachings herein.

Figure 5:
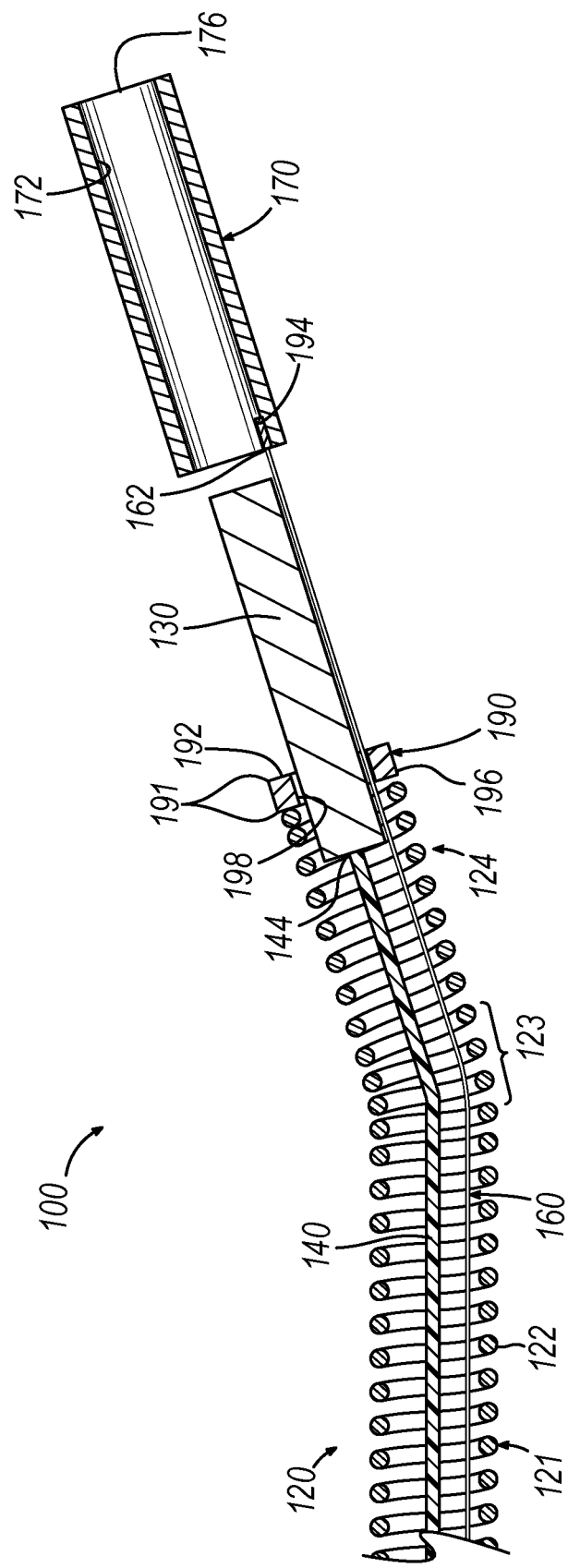
FIG. 5 depicts an enlarged side cross-sectional view of the distal portion of the guidewire of FIG. 4 taken along a centerline thereof, having a core wire soldered between the outer coil and a hypotube.

FIG. 5 shows the outer coil assembly (120) fitted with the position sensor (130) and communication wire (140). The core wire (160) is soldered to the outer coil proximal portion (126) (see FIG. 2) and to the hypotube inner diameter (172). The position sensor (130) is coaxially aligned with the hypotube inner diameter (172).

Figure 6:
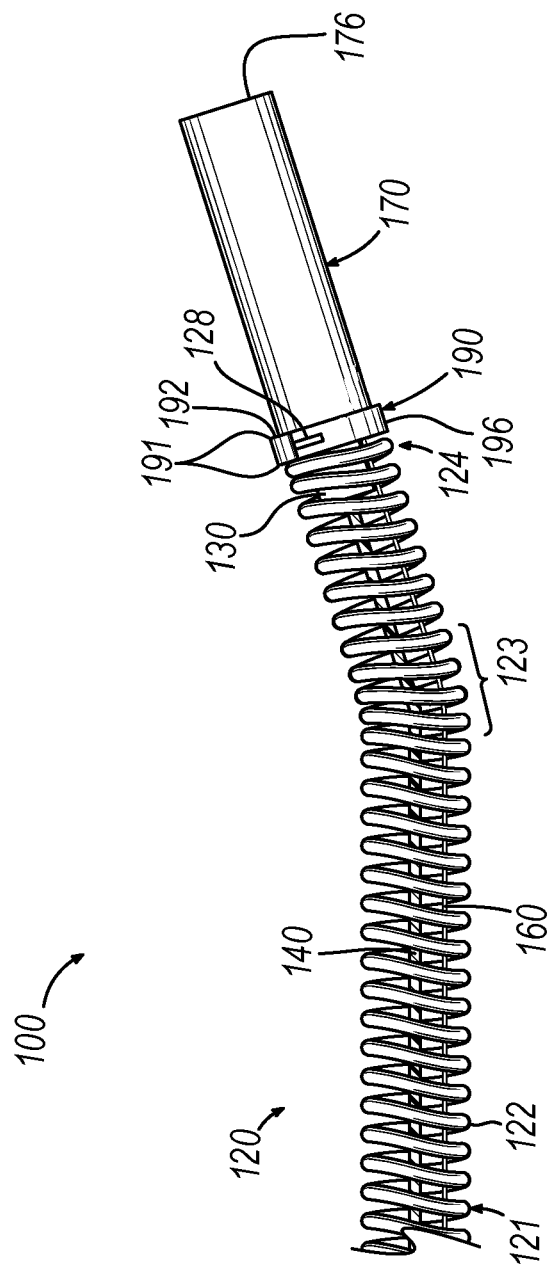
FIG. 6 depicts an enlarged side elevational view of the distal portion of the guidewire of FIG. 5 after being fitted with the hypotube.

FIG. 6 shows the hypotube (170) being affixed to the distal coil retainer (190). The hypotube (170) may be attached to the distal coil retainer (190) by soldering, welding, gluing, threading, or otherwise. The distal coil retainer (190) may have a distal retainer distal face (192) or a recess (not shown) that gives the solder (194) (see FIG. 5), weld (not shown), or glue (not shown) a place to adhere the hypotube (170) to the distal coil retainer (190). The hypotube (170) may additionally be attached to the distal coil retainer (190) with a fastener (128), via complementary threading, via a snap fitting, or in any other suitable fashion.

Figure 7:
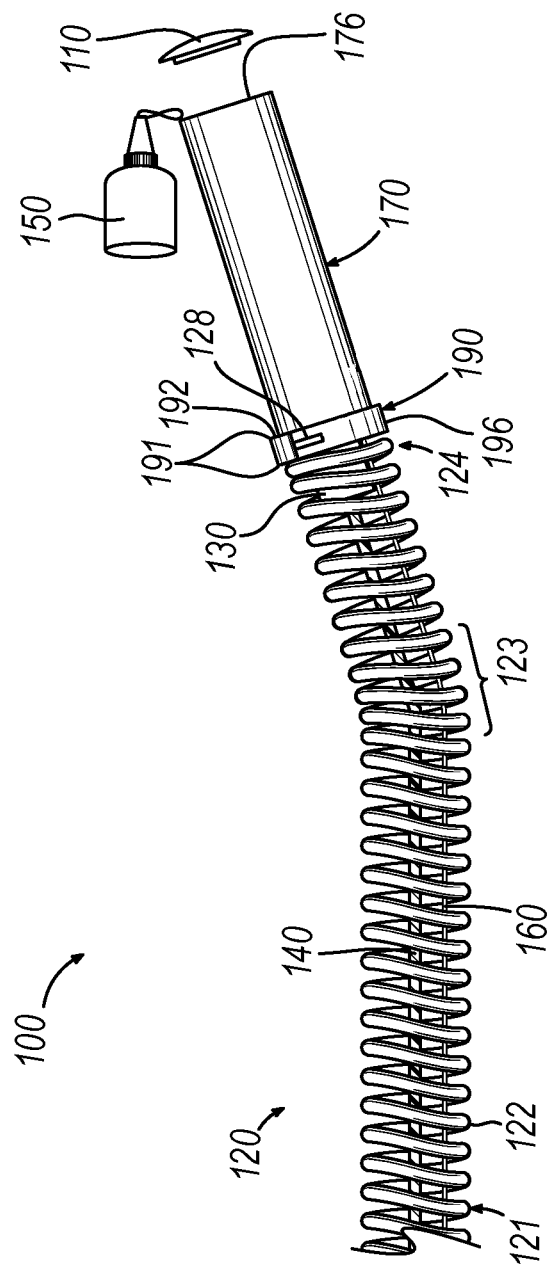
FIG. 7 depicts an enlarged side elevational view of the distal portion of the guidewire of FIG. 6 having the atraumatic tip glued to the hypotube.

FIG. 7 shows adhesive (150) being applied to the atraumatic tip (110). The adhesive (150) of the present example includes instant glue, though any other suitable form of adhesive (150) may be used. The adhesive (150) is applied to the proximal tip portion (112) (see FIG. 9) along the external diameter of the shaft (116) (see FIG. 9). The adhesive (150) is also applied to the proximal face (119) (see FIG. 9) of the distal tip portion (114) (see FIG. 9). The proximal tip portion (112) (see FIG. 9) is inserted into the hypotube inner diameter (172) (see FIG. 5). The atraumatic tip (110) may be held within the hypotube (170) until the instant glue (150) dries.

Figure 8:
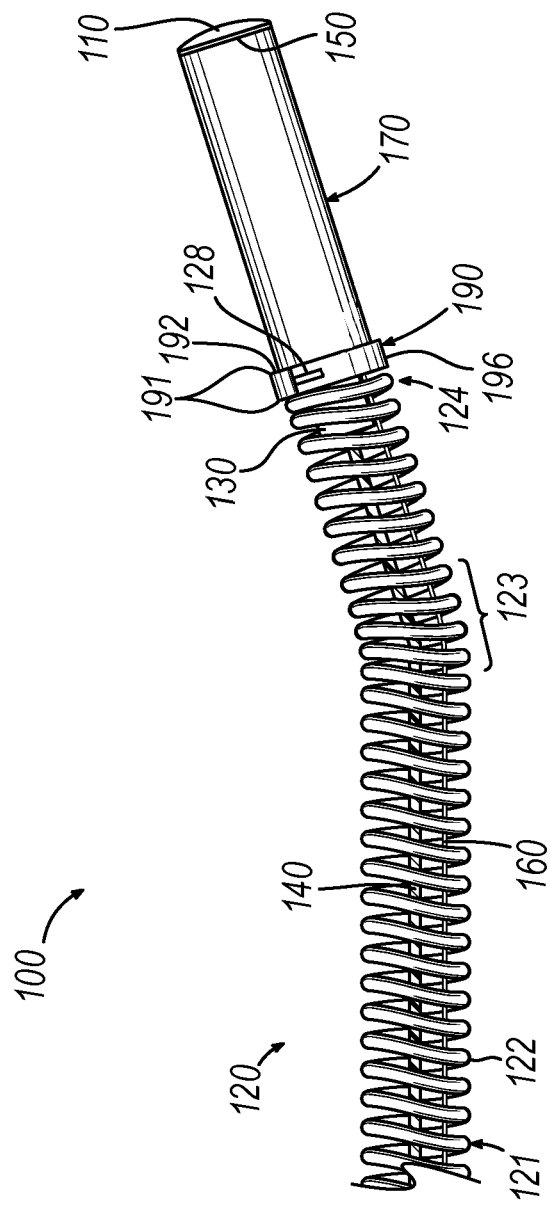
FIG. 8 depicts an enlarged side elevational view of the distal portion of the guidewire of FIG. 7 fitted with the atraumatic tip.

FIG. 8 shows a fully assembled guidewire (100) with an atraumatic tip (110) installed with instant glue (150). Once the adhesive (150) dries or otherwise cures, the guidewire (100) may be inspected. Once fully assembled, the process of allowing the adhesive (150) to dry or otherwise cure may take approximately 10 minutes or less. Once the adhesive (150) dries or otherwise cures, the guidewire (100) is inspected. In some instances, allowing the adhesive (150) to dry or otherwise cure, and the inspection of the atraumatic tip (110) inclusive, is approximately 10 minutes or less.

IV. Exemplary Atraumatic Tips

Figure 10:
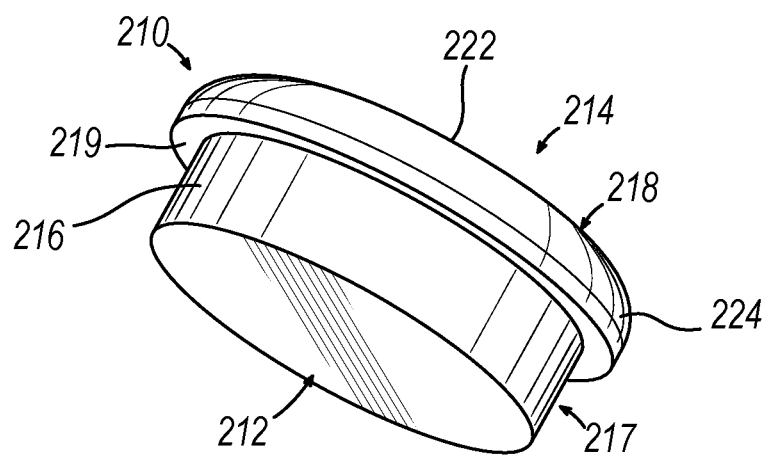
FIG. 10 depicts an enlarged perspective view of another exemplary atraumatic tip for the guidewire of FIG. 2.

FIGS. 9-10 show different types of atraumatic tips (110, 210). Both atraumatic tips (110, 210) may have advantages over the contemporary epoxy atraumatic tips because the atraumatic tips (110, 210) may include less expensive materials, simplify the manufacturing processes, and reduce labor costs. Both atraumatic tips (110, 220) may be manufactured by stamping, injection molding, die casting, end forming, additive manufacturing, or machining from a solid piece. Additional machining and polishing may be required after stamping, injection molding, die casting, end forming, additive manufacturing, or machining from a solid piece.

FIG. 9 shows an atraumatic tip (110) including a hollow shaft (116). The atraumatic tip includes a proximal tip portion (112) and a distal tip portion (114). The proximal tip portion (112) includes a hollow shaft (116) having a shaft inside diameter (115) and a shaft outside diameter (117). The proximal portion extends distally to the distal tip portion (114). The distal tip portion (114) is mated to the proximal tip portion (112) at a proximal face (119) and extends distally through the arcuate portion (118) to a distal most tip (113). The arcuate portion (118) has an arcuate shape.

The atraumatic tip (110) has less weight and cost of bulk materials compared to an atraumatic tip (210) (see FIG. 10). The atraumatic tip (110) is constructed of a surgical safe metal such as stainless steel or aluminum. Alternatively, atraumatic tip (110) may be formed of a plastic or some other material(s). In some instances, the atraumatic tip (110) may be constructed by injection molding or die casting. After the injected material is poured in a mold (not shown), the atraumatic tip (110) is removed from the mold and allowed to cool. After the atraumatic tip (110) has cooled, the atraumatic tip (110) is further machined with a lathe (not shown) or a milling machine (not shown). After machining, the atraumatic tip (110) may be polished.

In other instances, the atraumatic tip (110) may be formed by end forming a hollow tube. After end forming the hollow tube, the distal most tip (113) may be welded, machined smooth, and polished. The atraumatic tip (110) is then severed from the hollow tube, the hollow tube is longitudinally advanced a set distance within the machine and another atraumatic tip (110) may be end formed from the remaining portion of the hollow tube.

FIG. 10 shows the atraumatic tip (210) having a solid shaft (216). The atraumatic tip (210) is like atraumatic tip (110) (see FIG. 9). The atraumatic tip (210) has a proximal tip portion (212) and a distal tip portion (214). The distal tip portion (214) has a blunt portion (218) and a proximal face (219). In this example, the blunt portion (218) has a flat surface (222) and a rounded edge (224), in comparison to the arcuate portion (118) that has an arcuate shape. The atraumatic tip (210) also differs from the atraumatic tip (110) because the atraumatic tip (210) includes a proximal tip portion (212) that has a solid shaft (216) and does not have an inside diameter (115) (see FIG. 9).

The atraumatic tip (210) may have advantages in some instances over the atraumatic tip (110). The atraumatic tip (210) may require fewer steps to manufacture than atraumatic tip (110). A piece of round stock (not shown) may be chucked in a lathe or similar machine. The atraumatic tip (210) is then machined. A finished atraumatic tip (210) may be parted from the piece of stock (not shown) with a cutting tool (not shown). The piece of stock (not shown) may be longitudinally advanced a set distance on the lathe or a similar machine. The machining operation may be quickly repeated. The similar machine may be a (computer numeric control) CNC machine. Automated machinery such as a CNC machine may further reduce the cost of labor to produce the atraumatic tip (210). After the atraumatic tip (210) is machined, the atraumatic tip (210) may be polished.

V. Exemplary Steps to Manufacture Guidewire with an Atraumatic Tip

Figure 2:
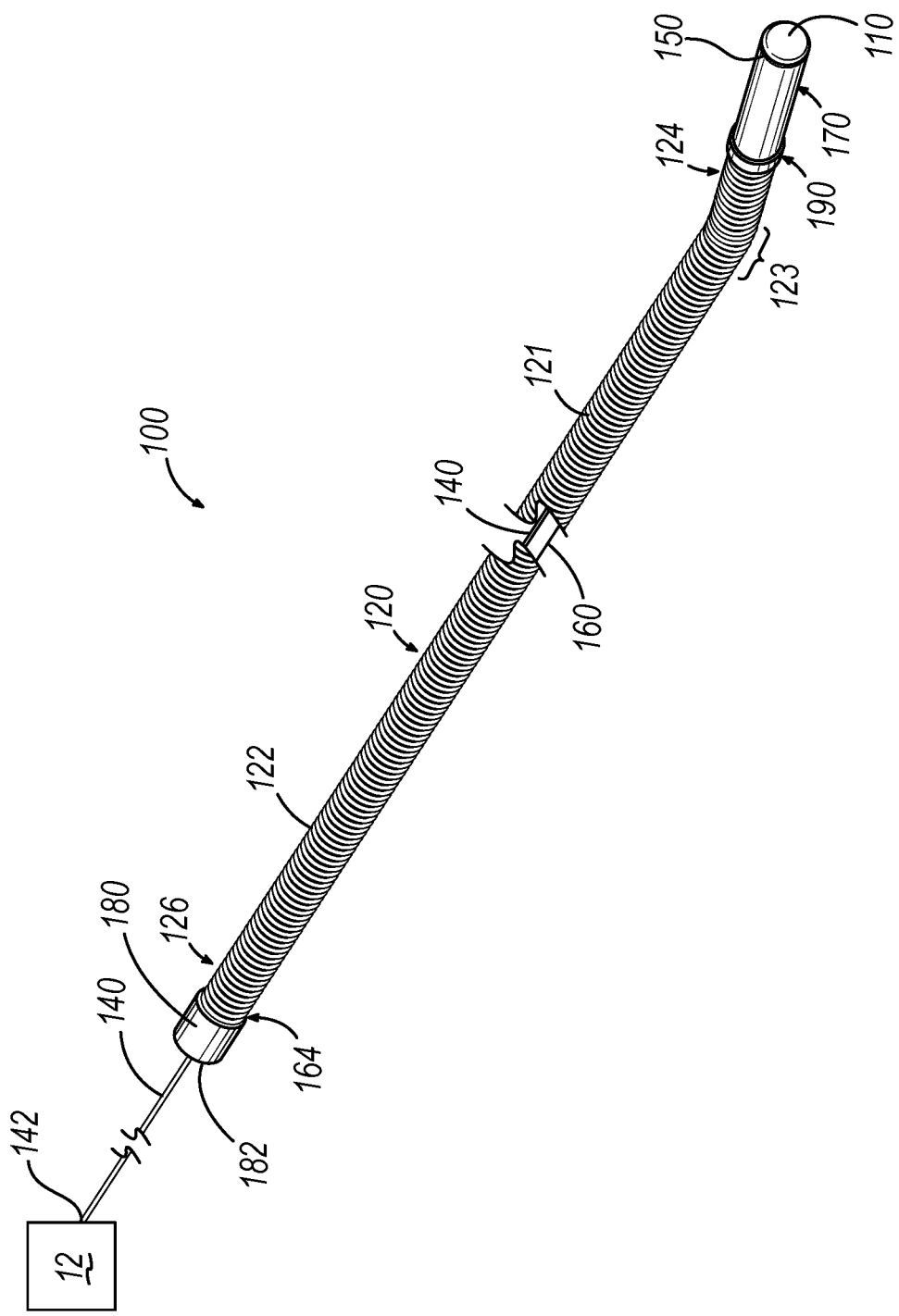
FIG. 2 depicts a perspective view of an exemplary guidewire connected to a processor of the system of FIG. 1.
Figure 3:
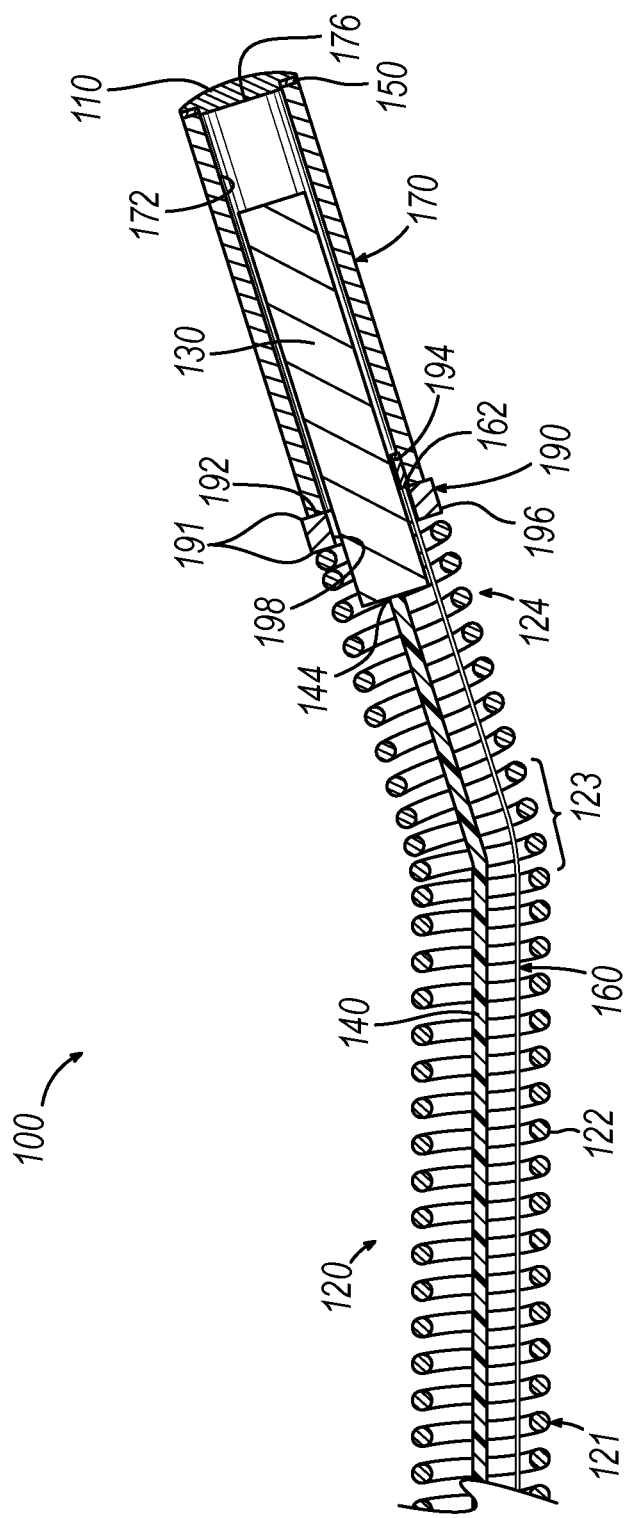
FIG. 3 depicts a side cross-sectional view of the distal portion of the guidewire of FIG. 2.
Figure 11:
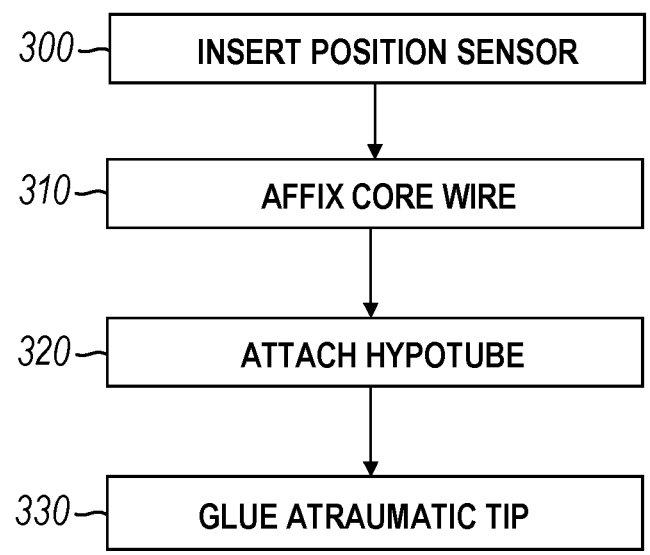
FIG. 11 depicts a flowchart depicting an example of a method of assembling the guidewire of FIG. 2.

FIG. 11 shows an exemplary set of steps of the method of manufacturing the guidewire (100) of FIG. 2 with the atraumatic tip (110) as detailed further above. As a first step, the position sensor (130) is inserted into the outer coil assembly (120) (block 300). After the position sensor (130) is inserted, the core wire (160) is affixed between a hypotube (170) and the outer coil assembly (120) (block 310). Next, the hypotube (170) is attached to the outer coil assembly (120) (block 320). Then, the atraumatic tip (110) is glued with instant glue (150) to the hypotube (170) (block 330).

VI. Assembly of Another Exemplary Guidewire with and Atraumatic Tip

Figure 12:
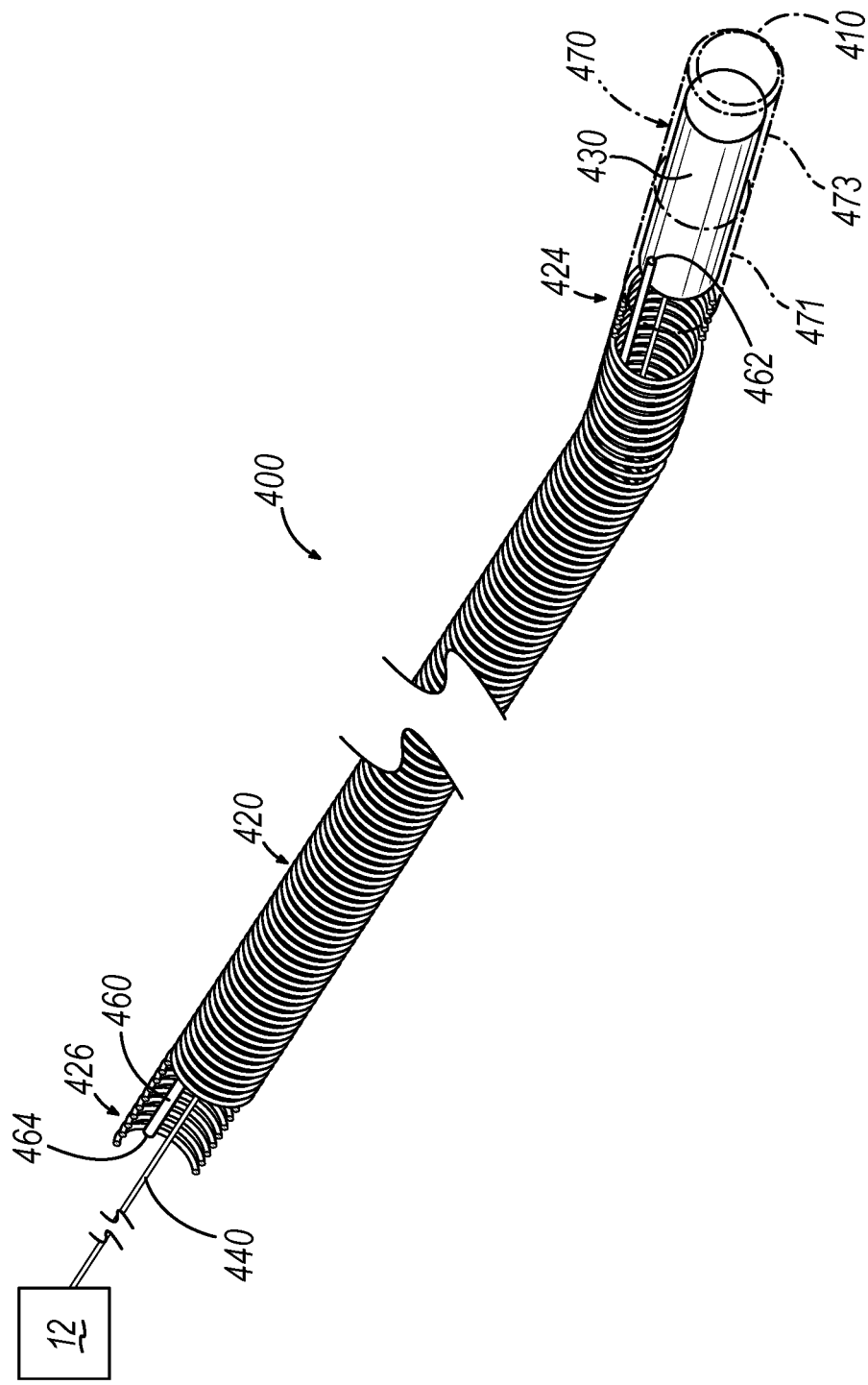
FIG. 12 depicts a perspective view of another exemplary guidewire connected to a processor of the system of FIG. 1.

FIG. 12 depicts another exemplary guidewire (400) similar to guidewire (100). The guidewire (400) of this example has features that allow a manufacturer to accurately and efficiently install an atraumatic tip (410) and position sensor (420). Such features may reduce the risk of damaging position sensor (420) during the manufacture of guidewire (400). The guidewire (400) of this example, like guidewire (100), has an outer coil assembly (420), a position sensor (430), a communication wire (440), an adhesive (450), and a core wire (460). The guidewire (400) of this example differs from guidewire (100) in that guidewire (400) has a two-part hypotube assembly (470) rather than the single piece hypotube (170) (see FIG. 2). The outer coil assembly (420) extends distally from an outer coil proximal portion (426) to an outer coil distal portion (424). The proximal hypotube (471) extends distally from the outer coil distal portion (424) to the distal hypotube (473). The distal hypotube (473) extends distally from the proximal hypotube (471) to the atraumatic tip (410). The proximal and distal hypotubes (471, 473) together contain the position sensor (430). The position sensor (430) is connected to the processor (12) via the communication wire (440). In the current example, the core wire (460) extends distally from the proximal portion of the outer coil assembly (426) to the hypotube assembly (470).

Figure 13:
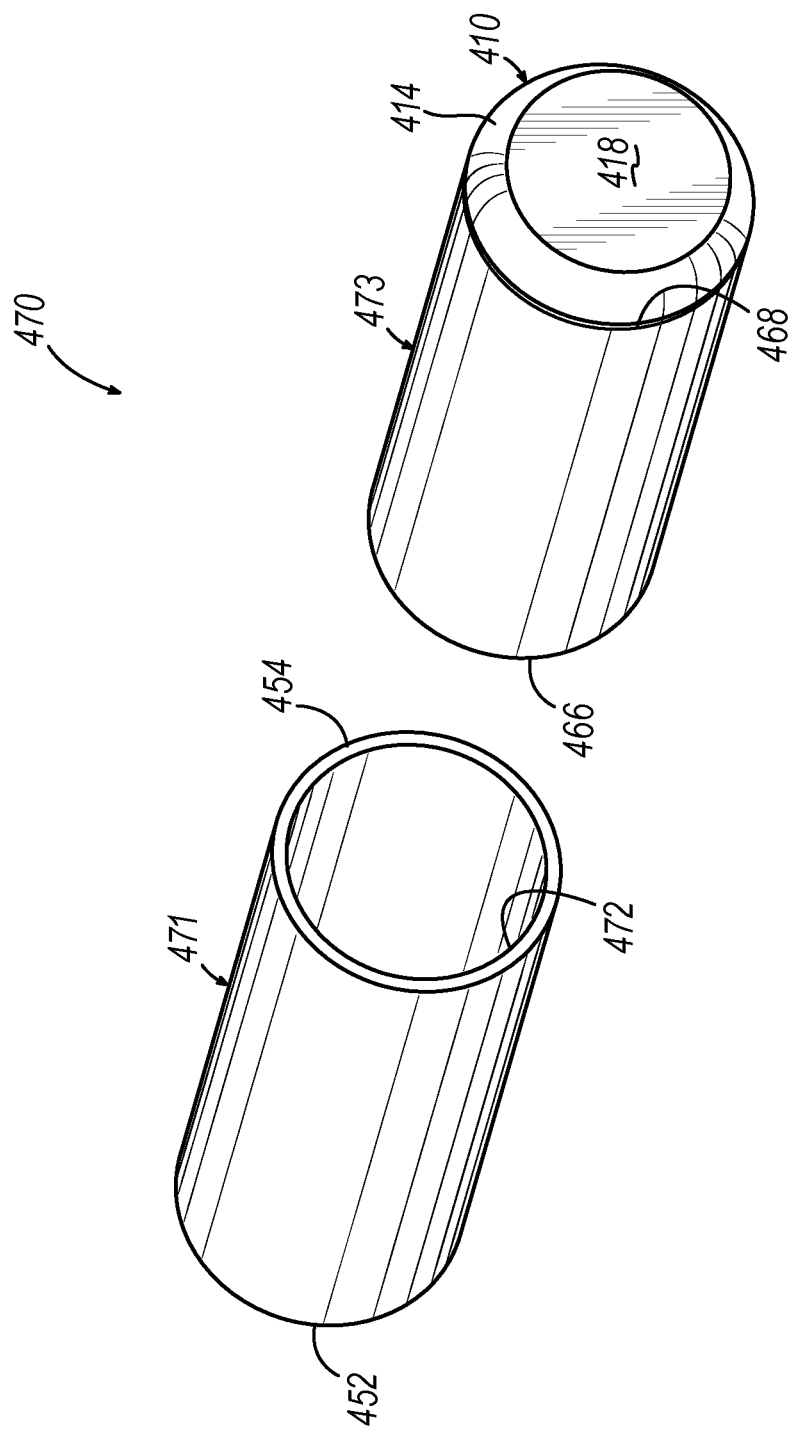
FIG. 13 depicts an enlarged perspective view of a hypotube assembly of the guidewire of FIG. 12.

FIG. 13 shows the hypotube assembly (470). The hypotube assembly (470) includes the proximal hypotube (471), the distal hypotube (473), and the atraumatic tip (410). Both the proximal hypotube (471) and the distal hypotube (473) are generally tubular and hollow like the hypotube (170) (see FIG. 2). Both the proximal and distal hypotubes (471, 473) are constructed of similar materials and methods to form as hypotube (170). The proximal hypotube (471) has a proximal end (452) that extends distally to a distal end (454). The distal hypotube (473) extends distally from a proximal end (466) to a distal end (468).

The atraumatic tip (410) is constructed of similar materials, methods to form, and characteristics as atraumatic tips (110, 210). Atraumatic tip (410) may include a proximal tip portion (not shown) and a distal tip portion (414). The proximal tip portion is similar to proximal tip portion (112, 212) and a distal tip portion (414) similar to distal tip portion (114, 214). The proximal tip portion (not shown) may have a shaft (not shown) similar to shaft (116, 216). The shaft may be hollow or solid. This shaft (not shown) is inserted into an interior diameter of distal hypotube (473) to aid in centering and retaining the atraumatic tip (410) within the hypotube assembly (470). The atraumatic tip (410) may be soldered, welded, or brazed to the hypotube assembly (470). The atraumatic tip may also be glued with an adhesive (150) (see FIG. 7). In the current version, the atraumatic tip (410) is laser welded to the distal hypotube (473). Alternatively, any other suitable techniques may be used to secure atraumatic tip (410) to distal hypotube (473).

The distal tip portion (414) may have an arcuate portion (not shown) similar to the arcuate portion (118) or a blunt portion (418) similar to blunt portion (218). In some versions, the atraumatic tip (410) may not have a proximal tip portion (not shown) and the distal tip portion (414) may be soldered, welded, or brazed directly to a distal end (476) of the distal hypotube (473); or otherwise secured to distal end (476) of distal hypotube (473).

FIG. 14 shows the core wire (460) attached to the hypotube assembly (470). The core wire may be attached by welding, soldering, or brazing. The core wire (460) includes a proximal and distal end (464, 462). The core wire (460) has similar properties and functions as core wire (160) and may thus prevent longitudinal stretching of guidewire (400) during normal operation of guidewire (400). The core wire proximal end (464) (see FIG. 12) is attached to the proximal end (426) of the outer coil assembly (420). The core wire distal end (462) is attached to the hypotube assembly (470). In the current version, the core wire distal end (462) is soldered (or otherwise secured) to the inner diameter (472) of the proximal hypotube (471). Alternatively, the core wire distal end (462) may be soldered (or otherwise secured) to distal hypotube (473).

In some versions, one or more additional core wires (not shown) may attach the proximal hypotube (471) to the distal hypotube (473). The additional core wires may have the same non-extensible properties and functions as the core wire (460). In yet other versions, the core wire distal end (462) is attached to the interior diameter (472) of the distal hypotube (473). In still other versions, the core wire (460) is attached to both the proximal and distal hypotube (471, 473).

FIG. 15 shows the proximal hypotube (471) extending distally from a distal portion (424) of the outer coil assembly (420). The proximal hypotube (471) may be attached to the distal portion (424) of the outer coil assembly (420) by welding, soldering, brazing, and adhesive; or using any other suitable techniques. The outer coil assembly (420) may include components similar to the outer coil assembly (120) such as an outer coil (122), a proximal coil retainer (180), and a distal coil retainer (190). The outer coil assembly (420) may be constructed of components that have resilient yet flexible properties that are apparent to those skilled in the art in view of the teachings herein. Such an outer coil assembly (420) allows an operator to guide a larger instrument such as a catheter for an operation within or adjacent to various anatomical passageways of the body.

The proximal hypotube (471) may have a provision (not shown) that aids in axially and radially attaching the proximal end (452) of proximal hypotube (471) to the distal portion of outer coil assembly (424). The provision may be located on the proximal hypotube (471), with a complementary provision on the distal portion (424) of the outer coil assembly (420). The provisions are configured to quickly and easily attach the proximal hypotube (471) to the distal portion (424) of the outer coil assembly (420). The provision may include a retainer, an adhesive (150) (see FIG. 7), or some other fastener that allows the proximal hypotube (471) to axially and radially fasten the distal portion (424) (see FIG. 15) of the outer coil assembly (420) to the proximal end (452) of the hypotube (471). Examples of various forms that such a provision may take will be apparent to those skilled in the art in view of the teachings herein.

Figure 16:
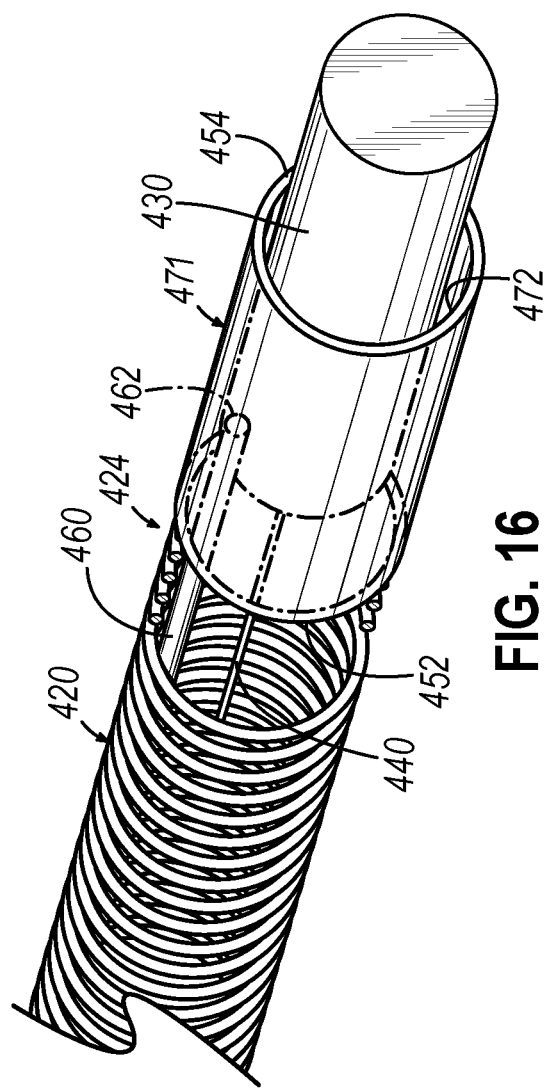
FIG. 16 depicts a perspective view of the hypotube assembly, core wire, and outer coil assembly of FIG. 15 with a position sensor inserted and glued into the proximal hypotube.

FIG. 16 shows the guidewire (400) with the position sensor (430) being partially inserted and glued into the hypotube (471). The position sensor (430) is glued with an adhesive (150) in this example, though any other suitable methods may be used to secure position sensor (430) relative to proximal hypotube (471). The adhesive (150) may include an instant glue. The position sensor (430) of this example, like position sensor (130), is in communication with the processor (12) (see FIG. 12) via the communication wire (440) (see FIG. 12). The position sensor (430) is configured to generate signals in response to an alternating electromagnetic field generated by field generator (24) (see FIG. 1), with such signals being indicative of the location of the position sensor (430) (and, hence, the distal end of guidewire (100)) within the head (H) of the patient (P). At the stage of assembly shown in FIG. 16, approximately half of the length of position sensor (430) is positioned within proximal hypotube (471) while the other half of the length of position sensor (430) protrudes distally from proximal hypotube (471). Alternatively, any other suitable portion of the length of position sensor (430) may be positioned within proximal hypotube (471) at this stage of assembly.

Figure 17:
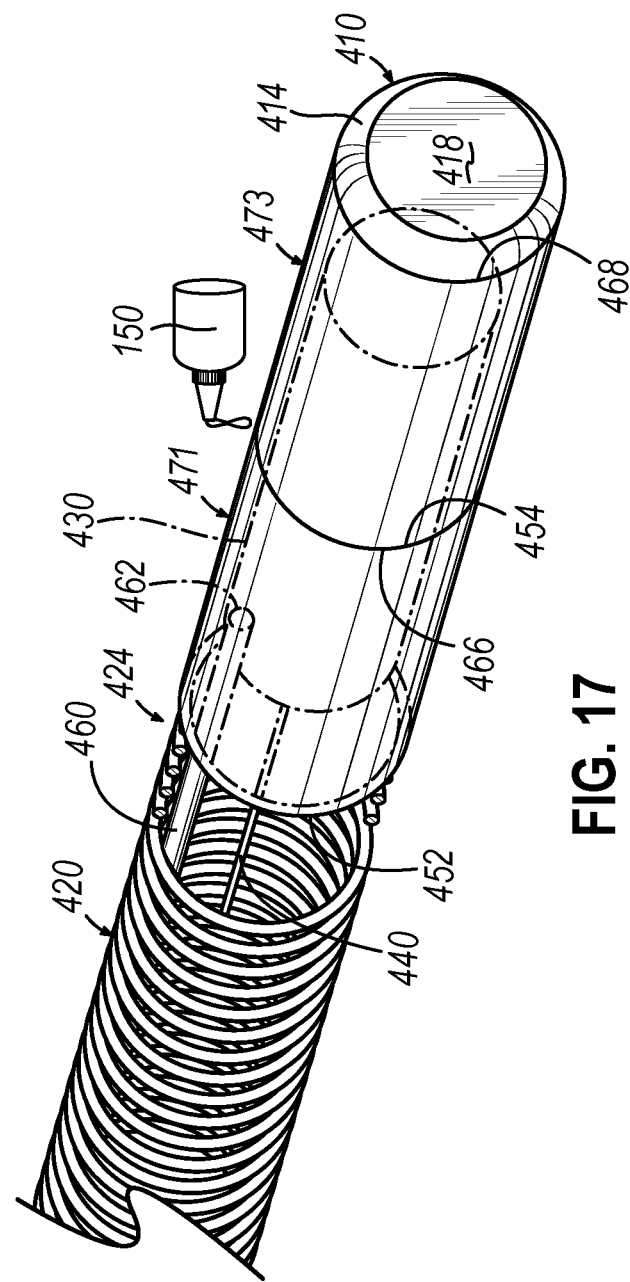
FIG. 17 depicts a perspective view of the hypotube assembly, core wire, outer coil assembly, and position sensor of FIG. 16 with a distal hypotube glued to the proximal hypotube.

FIG. 17 shows the guidewire (400) with the proximal end (474) of distal hypotube (473) being glued to the distal end (454) of the proximal hypotube (471). The position sensor (430) is encapsulated by the proximal and distal hypotubes (471, 473). In versions with the core wire (460) attached to the distal hypotube (473), the core wire (460) is attached to the distal hypotube (473) before the distal end of the proximal hypotube (471) is secured to the proximal end of the distal hypotube (473). The proximal hypotube (471) may have a provision (not shown) for attaching the proximal end (466) of the distal hypotube (473) to the distal end (454) of the proximal hypotube (471) similar to the provision that may attach the proximal end (474) of proximal hypotube (471) to the distal portion (424) of the outer coil assembly (420). In this example, hypotubes (471, 473) are joined together in an end-to-end fashion. In some other versions, distal hypotube (473) slides over the exterior of proximal hypotube (471) and thereby encapsulates at least some of the length of proximal hypotube (471) (if not the entire length of proximal hypotube (471)).

VII. Steps to Manufacture Another Guidewire with an Atraumatic Tip

Figure 18:
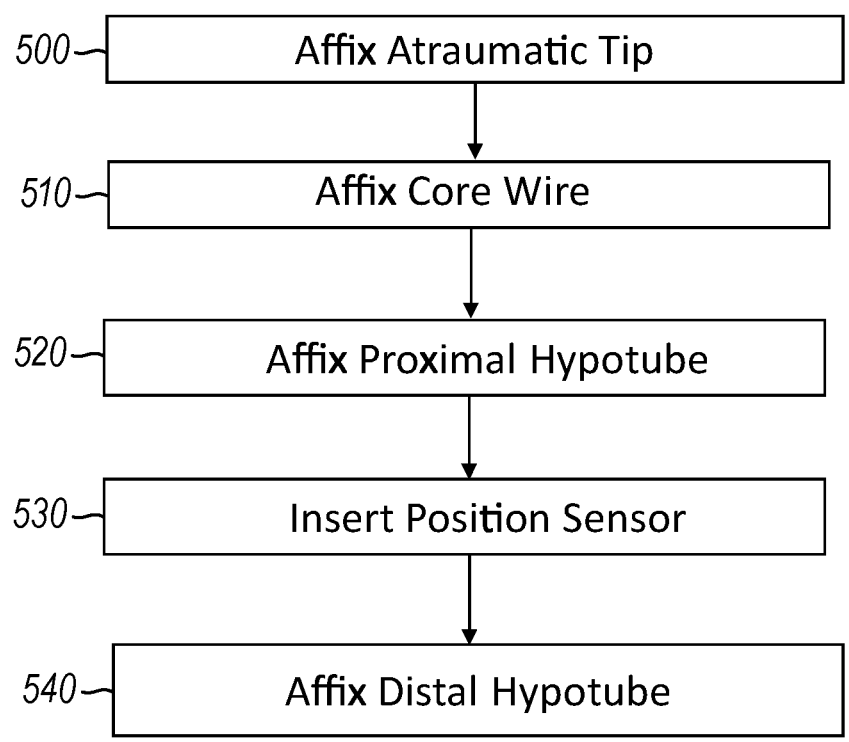
FIG. 18 depicts a flowchart depicting an example of a method of assembling the guidewire of FIG. 12.

FIG. 18 shows an exemplary set of steps of the method of manufacturing the guidewire (400) of FIG. 12 with the atraumatic tip (410) and hypotube assembly (470) as detailed further above. As a first step, the atraumatic tip (410) is secured (e.g., welded, brazed, soldered, adhered, etc.) to the distal end (476) of the distal hypotube (473) (block 500). The core wire (460) is secured (e.g., welded, brazed, soldered, adhered, etc.) to the proximal hypotube (471) (block 510). After the core wire (460) is secured to the proximal hypotube (471), the proximal hypotube (471) is secured (e.g., welded, brazed, soldered, adhered, etc.) to the distal portion (424) of the core wire assembly (420) (block 520). The position sensor (430) is inserted and secured (e.g., glued, etc.) within the proximal hypotube (471) (block 530). Next, the proximal end (474) of the distal hypotube (473) is secured (e.g., welded, brazed, soldered, adhered, etc.) to the distal end (454) of the proximal hypotube (471) (block 540).

In the present example, position sensor (430) is assembled into guidewire (400) in an isolated enclosure (i.e., hypotube assembly (470)) without introducing any heat that could otherwise damage position sensor (430). In versions where adhesive (450) is instant glue, this method of assembly may avoid the potentially undesirable use of conductive glue, black epoxy, etc.; without compromising the integrity or durability of guidewire (400).

VIII. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A method of manufacturing a surgical guidewire, wherein the surgical guidewire includes: (i) an outer coil assembly, wherein the outer coil assembly has an outer coil that extends from a proximal coil retainer to a distal coil retainer, (ii) a position sensor, wherein the position sensor is located distally within the outer coil assembly, (iii) a communication wire, wherein the position sensor is configured to be in communication with a processor via the communication wire, (iv) an adhesive, (v) a core wire, (vi) a hollow tube, wherein the core wire extends distally from a proximal end of the outer coil to the hollow tube, and (vii) an atraumatic tip, the method comprising affixing the atraumatic tip to a distal end of the hollow tube with an adhesive.

Example 2

The method of Example 1, wherein the adhesive includes instant glue.

Example 3

The method of any one or more of Examples 1 through 2, wherein the atraumatic tip is constructed of a material that is a metal or a polymer.

Example 4

The method of any one or more of Examples 1 through 3, further comprising forming the atraumatic tip by stamping.

Example 5

The method of any one or more of Examples 1 through 3, further comprising forming the atraumatic tip by injection molding.

Example 6

The method of any one or more of Examples 1 through 3, further comprising forming the atraumatic tip by die casting.

Example 7

The method of any one or more of Examples 1 through 3, further comprising forming the atraumatic tip by end forming a tube.

Example 8

The method of any one or more of Examples 1 through 3, further comprising forming the atraumatic tip by additive manufacturing.

Example 9

The method of any one or more of Examples 1 through 3, further comprising forming the atraumatic tip by machining the atraumatic tip from a solid piece of the material.

Example 10

The method of any one or more of Examples 4 through 8, further comprising machining the atraumatic tip.

Example 11

The method of any one or more of Examples 4 through 10, further comprising polishing the atraumatic tip.

Example 12

The method of any one or more of Examples 1 through 11, wherein affixing the atraumatic tip to the distal end of the hollow tube takes approximately 10 minutes or less.

Example 13

The method of Example 12, further comprising inspecting the atraumatic tip, wherein the steps of affixing and inspecting together take approximately 10 minutes or less.

Example 14

The method of any one or more of Examples 1 through 13, further comprising connecting the communication wire to the position sensor.

Example 15

The method of Examples 1 through 14, further comprising installing the communication wire and position sensor within the outer coil.

Example 16

The method of Examples 1 through 15, further comprising affixing the hollow tube to the core wire.

Example 17

The method of Examples 1 through 16, further comprising affixing the core wire to the proximal end of the outer coil.

Example 18

The method of Examples 1 through 17, further comprising affixing the hollow tube to the distal end of the outer coil assembly.

Example 19

A method of manufacturing a surgical guidewire, wherein the surgical guidewire includes: (i) an outer coil assembly, wherein the outer coil assembly has a proximal portion and a distal portion, (ii) a position sensor, (iii) an adhesive, (iv) a core wire, and (v) a hollow tube assembly having: (A) a proximal tube, (B) a distal tube, and (C) an atraumatic tip; the method comprising: (a) securing the atraumatic tip to a distal end of the distal tube; (b) securing the distal end of the core wire to the proximal tube; (c) securing the proximal tube to a distal portion of the outer coil assembly; (d) securing a proximal end of the core wire to the proximal portion of the outer coil assembly; (e) securing the position sensor within the proximal tube; and (f) securing the proximal end of the distal tube to the distal end of the proximal tube.

Example 20

A method of manufacturing a surgical guidewire, wherein the surgical guidewire includes: (i) an outer coil assembly, wherein the outer coil assembly has an outer coil that extends from a proximal coil retainer to a distal coil retainer, (ii) a position sensor, wherein the position sensor is located distally within the outer coil assembly, (iii) a communication wire, wherein the position sensor is configured to be in communication with a processor via the communication wire, (iv) a core wire, (v) a hollow tube, wherein the core wire extends distally from a proximal end of the outer coil to the hollow tube, and (vi) an atraumatic tip, the method comprising: (a) connecting the communication wire to the position sensor; (b) installing the communication wire and the position sensor within the outer coil; (c) soldering, brazing, or welding a proximal of the core wire to the proximal end of the outer coil assembly; (d) soldering, brazing, or welding a distal end of the core wire to the hollow tube; (e) affixing the hollow tube to a distal end of the outer coil; and (f) gluing the atraumatic tip to the distal end of the hollow tube with an instant adhesive.

IX. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method of manufacturing a surgical guidewire, the surgical guidewire including:
   (i) an outer coil assembly, the outer coil assembly having an outer coil that extends from a proximal coil retainer to a distal coil retainer, wherein the distal coil retainer is mechanically coupled with the outer coil with a fastener,
   (ii) a position sensor, the position sensor being located distally within the outer coil assembly,
   (iii) a communication wire, the position sensor being configured to be in communication with a processor via the communication wire,
   (iv) an adhesive,
   (v) a core wire,
   (vi) a hollow tube, the core wire extending distally from a proximal end of the outer coil to the hollow tube, and
   (vii) an atraumatic tip,
   the method comprising:
   (a) inserting the position sensor into the outer coil assembly;
   (b) affixing the core wire between the hollow tube and the outer coil assembly after the step of inserting the position sensor into the outer coil assembly;
   (c) attaching the hollow tube mechanically to the outer coil assembly with the distal coil retainer after the step of affixing the core wire between the hollow tube and the outer coil assembly; and
   (d) affixing the atraumatic tip to a distal end of the hollow tube with the adhesive after the step of attaching the hollow tube to the outer coil assembly.

2. The method of claim 1, the adhesive including instant glue.

3. The method of claim 1, further comprising connecting the communication wire to the position sensor.

4. The method of claim 1, further comprising installing the communication wire within the outer coil.

5. The method of claim 1, the atraumatic tip being constructed of a material that is a metal or a polymer.

6. The method of claim 5, further comprising forming the atraumatic tip by stamping.

7. The method of claim 6, further comprising machining the atraumatic tip.

8. The method of claim 6, further comprising polishing the atraumatic tip.

9. The method of claim 5, further comprising forming the atraumatic tip by injection molding.

10. The method of claim 5, further comprising forming the atraumatic tip by die casting.

11. The method of claim 5, further comprising forming the atraumatic tip by end forming a tube.

12. The method of claim 5, further comprising forming the atraumatic tip by additive manufacturing.

13. The method of claim 5, further comprising forming the atraumatic tip by machining the atraumatic tip from a solid piece of the material.

14. The method of claim 1, the step of affixing the atraumatic tip to the distal end of the hollow tube taking 10 minutes or less.

15. The method of claim 14, further comprising inspecting the atraumatic tip, the steps of affixing and inspecting together take 10 minutes or less.

16. A method of manufacturing a surgical guidewire, the surgical guidewire including:
(i) an outer coil assembly, the outer coil assembly having an outer coil extending from a proximal coil retainer to a distal coil retainer,
(ii) a position sensor, the position sensor being located distally within the outer coil assembly,
(iii) a communication wire, the position sensor being configured to be in communication with a processor via the communication wire,
(iv) a core wire, the core wire having a first end and a second end,
(v) a hollow tube, the core wire extending distally from a proximal end of the outer coil to the hollow tube, and
(vi) an atraumatic tip,
the method comprising:
(a) connecting the communication wire to the position sensor;
(b) installing the communication wire and the position sensor within the outer coil after the step of connecting the communication wire to the position sensor;
(c) soldering, brazing, or welding the first end of the core wire to the proximal end of the outer coil;
(d) soldering, brazing, or welding the second end of the core wire to the hollow tube;
(e) affixing the hollow tube to the distal coil retainer after the steps of soldering, brazing, or welding the first end of the core wire to the proximal end of the core wire and the second end of the core wire to the hollow tube;
(f) applying instant adhesive to an external diameter of the atraumatic tip after the step of affixing the hollow tube to a distal end of the outer coil assembly; and
(g) inserting the external diameter of the atraumatic tip into an inner diameter of the hollow tube.

17. A method of manufacturing a surgical guidewire, the surgical guidewire including:
(i) an outer coil assembly, the outer coil assembly having an outer coil that extends from a proximal coil retainer to a distal coil retainer, wherein the distal coil retainer includes a mechanical fastener,
(ii) a position sensor, the position sensor being located distally within the outer coil assembly,
(iii) a communication wire, the position sensor being configured to be in communication with a processor via the communication wire,
(iv) a core wire,
(v) a hollow tube, the core wire extending distally from a proximal end of the outer coil to the hollow tube, and
(vi) an atraumatic tip,
the method comprising:
(a) connecting the communication wire to the position sensor;
(b) installing the position sensor within the outer coil after connecting the communication wire to the position sensor;
(c) soldering, brazing, or welding the core wire to the proximal end of the outer coil and the hollow tube;
(d) affixing the hollow tube to the distal coil retainer with the mechanical fastener after the steps of soldering, brazing, or welding the core wire to the outer coil and hollow tube;
(f) applying instant adhesive to an external diameter of the atraumatic tip after affixing the hollow tube to the distal coil retainer with the mechanical fastener; and
(g) inserting the external diameter of the atraumatic tip into an inner diameter of a hollow tube tip after the step of affixing the hollow tube to a distal end of the outer coil assembly.

* * * * *